(12) United States Patent
Epperson

(10) Patent No.: US 9,874,547 B2
(45) Date of Patent: Jan. 23, 2018

(54) WIRELESS COMBUSTION/EFFICIENCY ANALYZER

(71) Applicant: Fluke Corporation, Everett, WA (US)

(72) Inventor: David L. Epperson, Everett, WA (US)

(73) Assignee: Fluke Corporation, Everett, WA (US)

( * ) Notice: Subject to any disclaimer, the term of this patent is extended or adjusted under 35 U.S.C. 154(b) by 729 days.

(21) Appl. No.: 14/473,666

(22) Filed: Aug. 29, 2014

(65) Prior Publication Data
US 2016/0061799 A1    Mar. 3, 2016

(51) Int. Cl.
*G01L 7/00* (2006.01)
*G01N 33/00* (2006.01)
*G01K 13/02* (2006.01)

(52) U.S. Cl.
CPC ......... *G01N 33/0032* (2013.01); *G01K 13/02* (2013.01); *G01N 33/0062* (2013.01); *G01N 33/0075* (2013.01); *G01K 2013/024* (2013.01)

(58) Field of Classification Search
CPC ............. G01N 2030/025; G01N 30/74; G01N 33/225; G01N 35/00871; G01N 33/0062; G01K 13/02; G01K 2013/024
See application file for complete search history.

(56) References Cited

U.S. PATENT DOCUMENTS

| | | | |
|---|---|---|---|
| 3,831,430 A * | 8/1974 | Azinger, Jr. ........... | G01N 25/70 218/68 |
| 6,386,014 B1 * | 5/2002 | Butch ................ | G01N 30/6095 73/23.22 |
| 6,642,720 B2 | 11/2003 | Maylotte et al. | |
| 6,983,640 B1 | 1/2006 | Staphanos et al. | |
| 7,127,935 B2 | 10/2006 | Bonne et al. | |
| 8,689,605 B2 | 4/2014 | Bailey | |
| 2002/0182552 A1 | 12/2002 | Nielsen et al. | |
| 2007/0139183 A1 | 6/2007 | Kates | |

(Continued)

FOREIGN PATENT DOCUMENTS

| | | |
|---|---|---|
| CN | 201928445 U | 8/2011 |
| DE | 10 2004 042 919 A1 | 2/2006 |
| WO | 2006/122548 A1 | 11/2006 |

OTHER PUBLICATIONS

XP-002753315—Database WPI, Week 201160, Thomson Scientific, London, GB; 2011, 1 pg.

(Continued)

*Primary Examiner* — Elias Desta
(74) *Attorney, Agent, or Firm* — Seed IP Law Group LLP

(57) ABSTRACT

A technician uses a wireless apparatus and system to vary air or fuel in the burner to optimize efficiency and safety. A wireless remote sensor unit has a probe in a flue to draw a sample of combustion gas from the flue for gas sensors and a temperature sensor. The sensors generate analog signals of gas identity, concentration and temperature that are converted to digital signals by an A-to-D converter. A wireless transceiver sends digital signals to a hand held unit or central computer via wireless transmission. The hand held unit receives the digital signals and displays an analysis of the signals. The analysis may be performed by any one of the remote sensor unit, the hand held unit, or the central computer. The wireless unit also receives control signals for the hand held unit or the central computer.

15 Claims, 3 Drawing Sheets

(56) References Cited

U.S. PATENT DOCUMENTS

2009/0040044 A1\* 2/2009 Chiao .................. A61B 5/0002
　　　　　　　　　　　　　　　　　　340/540
2012/0297868 A1\* 11/2012 Elkins ...................... B09B 1/00
　　　　　　　　　　　　　　　　　　73/152.31

OTHER PUBLICATIONS

European Search Report dated Feb. 2, 2016, in corresponding EP 15 18 2948, 9 pgs.

\* cited by examiner

WIRELESS COMBUSTION/EFFICIENCY ANALYZER

BACKGROUND

When fuel is burned to heat water in boiler or air in a heat exchanger, a fuel such as natural gas, propane, kerosene, heating oil or coal is combined with oxygen to release heat. Combustion is complete when a hydrocarbon fuel is converted into carbon dioxide and water. Incomplete and inefficient combustion may produce unused heat and byproducts of combustion including carbon monoxide, carbon dioxide, and oxides of nitrogen and sulfur. The presence of carbon monoxide not only indicates inefficient combustion but is also a safety hazard. The temperature of flue gas is inversely proportional to efficiency. An inefficient burner literally sends energy up the chimney. For reasons of safety, efficiency and regulatory compliance, it is important to monitor the temperature of the combined combustion gases in a flue as well as the types of gases produced and the concentration of each gas as a percent of the total of all combustion gases. Gas analyzers measure the efficiency of flue gas and identify the component gases in flue gas and the concentration of each component.

Over a period of operation, burners for boilers or hot air heating systems may become less efficient, unsafe or non-compliant with environmental regulations. In order to adjust the burner to maximize efficiency, safety and compliance, a technician uses a gas analyzer to measure the temperature of the flue gas and identify the types of gases and concentration of each gas in the flue gas. Using that information, a technician may adjust the relative and total amounts of fuel and air used by the burner to combust the fuel. While 100% efficiency is not possible, it is realistic to adjust burners to achieve close to 95% efficiency. High rise office buildings and high rise residences may have three or more boilers that consume thousands of gallons of heating fuel or thousands of cubic feet of natural gas. Even a small improvement of 2-3% in efficiency could save hundreds of thousands of dollars.

Conventional flue gas analyzers are often hand held devices with a sensor for temperature and multiple sensors of different types of gases and concentrations of gases. Combustion gas is sampled by inserting a probe into an access aperture of a flue. The probe is a long tube with a handle grip. The tube is in fluid communication with an outlet at the bottom of the handle. A flexible hose that is several feet long connects the outlet of the handle to a hand held gas analyzer. The analyzer has a pump with an inlet connected to the hose. The pump applies suction to the hose and draws a sample of flue gas into the analyzer. A filter is located between the outlet of the pump and the sensors. The gas sample passes through the filter which removes soot and other particulates that could damage sensitive temperature and gas sensors in the gas analyzer.

A technician inserts the probe into a flue and turns on the pump to acquire a sample of the flue gas. The gas analyzer displays the flue gas temperature, the types of gases in the sample, and the concentration for each component gas. With the probe in the flue and display in sight, the technician makes one or more adjustments to the burner, including changing the amount of air or fuel of both to maximize efficiency, minimize safety hazards, and comply with government regulations.

Conventional gas analyzers have a number of drawbacks that make it difficult for the technician to properly adjust the burner. Sometimes the probe slips out of the flue aperture and the process must be restarted. The pump is relatively small and slowly draws the gas sample which may cool before reaching the temperature sensor in the gas analyzer. Even if the hose is relatively short, some cooling is inevitable and the temperature reading is inaccurate. There may be insufficient space in the boiler room to simultaneously display the results and permit the technician to adjust the burner. For example, a hose short enough to minimize cooling may not be long enough to reach a location where the technician may see the display while making air and fuel adjustments. The foregoing are representative of problems addressed by the embodiments described in this patent.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A wireless gas analyzer system with a sensor unit solves a number of the problems of conventional gas sensors. The cooling problem is solved because the hose is eliminated and the temperature of the gas sample is taken at a location close to the flue.

The wireless sensor unit is more stable and held in place in the flue by the friction between a probe tube and a wall for the flue that surrounds an aperture that receives the probe tube. The pump and the sensors are contained in a housing that is proximate the flue aperture. The pump may be smaller than a conventional gas analyzer pump because the distance the sample travels outside the flue may be only a few inches. A wireless hand held unit with a display may be located at any convenient location chosen by a technician. The location of the hand held display during adjustment is not constrained by the length of the hose because the hose is eliminated.

The wireless gas analyzer system includes a wireless remote sensing unit and a wireless hand held unit. The sensing unit has a housing to hold component electronics, a pump, a filter and a probe tube. The probe tube has one end extending from the housing and through a wall of a flue into a bore of the flue. The pump has an inlet connected to the other end of the probe tube. The pump draws a sample of combustion gas from the flue and discharges the gas sample into the filter. A temperature sensor and one or more gas sensors are in fluid communication with the filter. Each gas sensor is configured to sense a presence of one or more gases in the filtered gas sample and to measure concentrations of each component gas. The gas and temperature sensors output analog signals are representative of the temperature, the identity of each gas, and the concentration of each gas. A wireless transceiver sends signals representative of temperature, type of gas and its concentration and receives control signals from a hand held unit.

In some embodiments, the remote sensor unit has a microprocessor and a memory. The microprocessor may be programmed to perform a number of supervisory functions, analysis and other operations. The microprocessor has a clock and may perform one or more operations based on sensed events, elapsed time between events, at periodic intervals, or combinations thereof. The microprocessor is connected to an analog-to-digital converter that converts analog output signals of the sensors into digital signals. The memory holds data acquired by the sensors, in particular digital data representative of the sensed temperature, gas type and gas concentration. A wireless transceiver is connected to the microprocessor. The wireless transceiver is a low power radio such as a Bluetooth Low Energy device. The transceiver communicates with another transceiver in the hand held unit or a central monitoring computer, or both. The wireless transceiver receives control information from the hand held unit, the central monitoring computer, or both, and passes the control information to the microprocessor. A replaceable or rechargeable power source, such as one or more batteries, provides power to the pump, the sensors, the microprocessor and other electronic components.

The hand held unit has a number of components including a microprocessor, a memory, a display, a keypad for entering input and command information, a wireless transceiver for receiving signals representative of temperature, types of gases and concentrations of gases and for transmitting control signals. The hand held unit also has a power source for supplying power to each of the components.

In some embodiments, the hand held unit has circuitry and software in the microprocessor or memory for issuing commands to the remote sensor unit. Such commands include directions to wake up, turn on the pump, take a series of readings of the sensors, and wirelessly transmit the results to the hand held unit. The remote sensor unit may remain powered up for a predetermined time that is adjustable in accordance with commands from the hand held unit.

In other embodiments, the remote sensor unit is programmed to periodically wake up, take readings of the sensors, and send the reading to the central control computer. Thereafter, the remote sensor unit will power down and wait for another command or a predetermined time for a next set of readings and transmissions.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
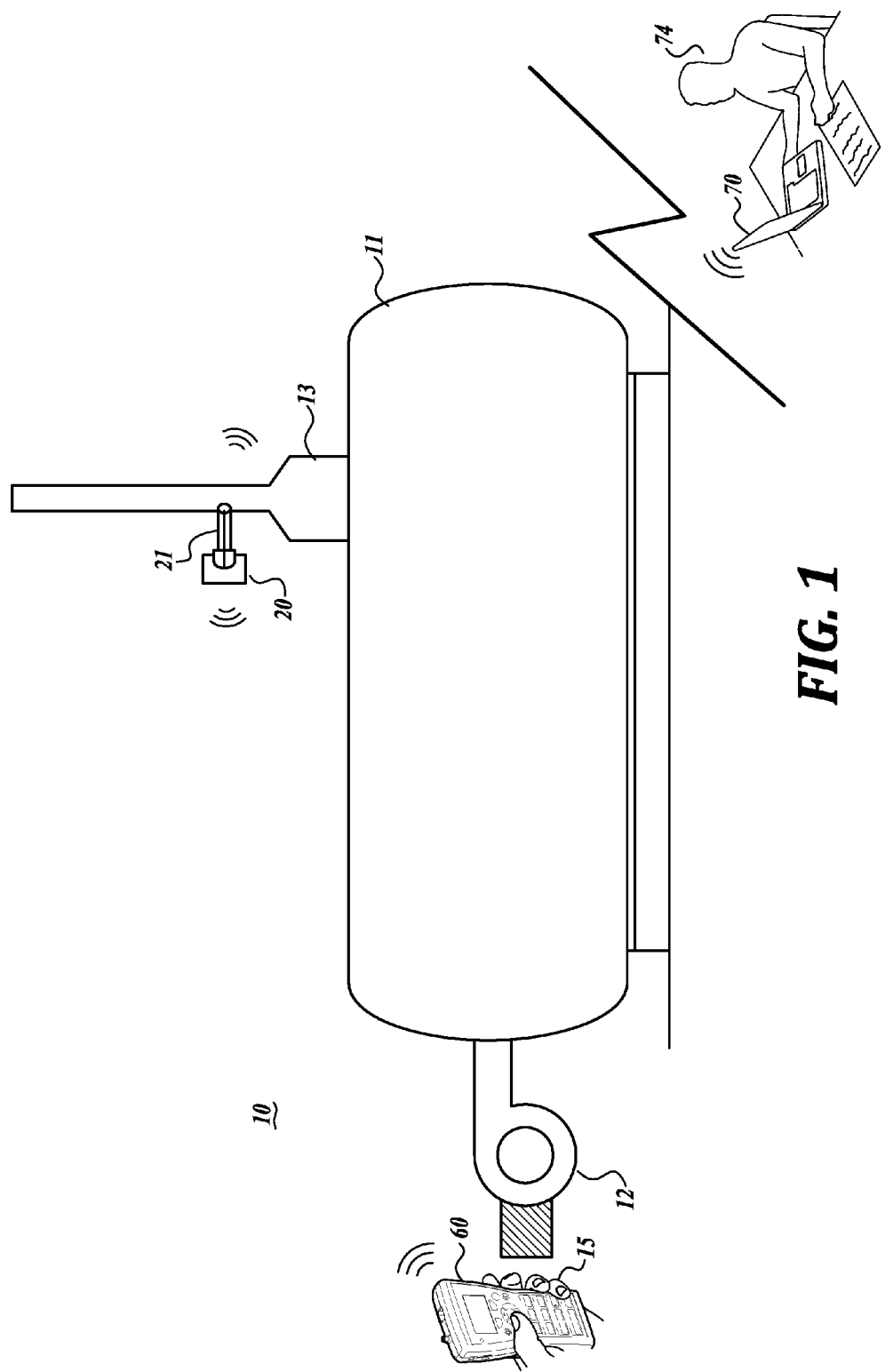
FIG. 1 is a schematic representation of a wireless gas analyzer system configured to take temperature and gas readings of combustion gases in a flue.

FIG. 1 shows a gas analyzer system 10 that may measure and record the efficiency of a burner 12 that heats water for a boiler 11. The burner 12 may rely upon one or more fuels, including and not limited to heating oil, natural gas, propane, kerosene, coal, or other hydrocarbon fuels. After the fuel is burned, combustion gas is discharged into the air through a chimney or flue 13. A wireless remote sensor unit 20 has a probe 21 that extends into the flue 13. Sensor unit 20 has one or more sensors for acquiring the temperature of gas in the flue and for identifying the types of gases and the respective concentrations of those gases that comprise the flue gas. Such gases may include and are not limited to carbon monoxide, carbon dioxide, and oxides of nitrogen and sulfur. Technician 15 attends the burner 12 and is equipped with wireless hand held gas analyzer unit 60. Technician 15 reads information on a display of the wireless hand held gas analyzer unit 60 to adjust the air intake and fuel intake of the burner to optimize efficiency and/or reduce amounts of unwanted combustions gases.

In an alternate embodiment, the wireless remote sensor unit 20 communicates with a remote central control computer 70 to provide information on the temperature of the flue gas, the gases that comprise the flue gas and the concentrations of those gases. Analyst 74 reviews the information from wireless remote sensor unit 20 and from other wireless remote sensor units attached to other flues that exhaust gas from other burners. The multiple wireless remote sensor units thus comprise a network of sensor units that is remotely monitored at a central computer 70 by analyst 74.

Figure 2:
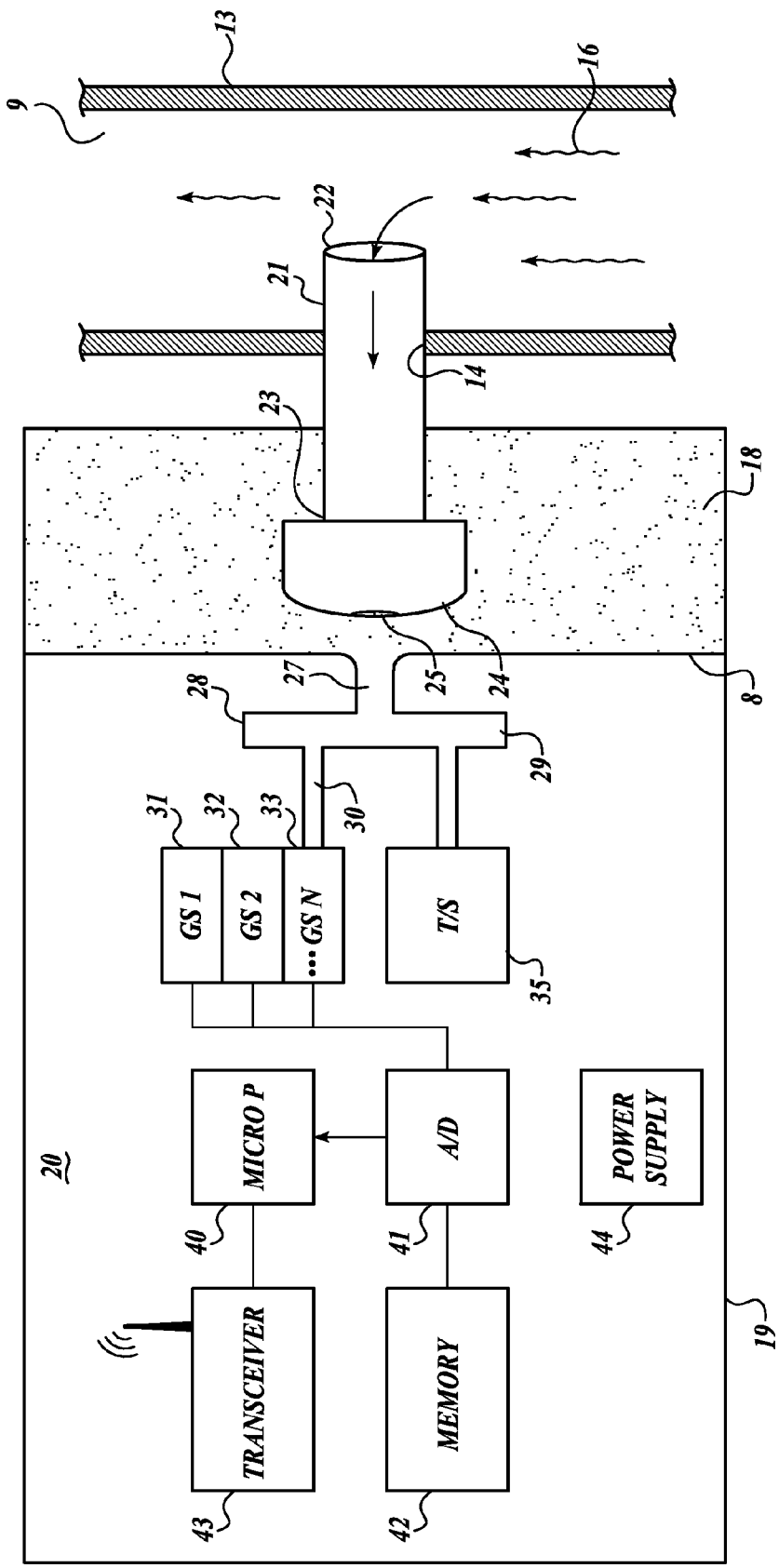
FIG. 2 is a schematic representation of one embodiment of a remote sensor unit.

With reference to FIG. 2, wireless remote sensor unit 20 has a housing 19. A probe 21 extends from the housing, through an aperture 14 in flue 13 and into bore 9 of flue 13. Flue 13 contains combustion gas 16. Probe tube 21 has an inlet 22 in bore 9 of flue 13. The other end 23 of the probe tube 21 is attached to inlet 22 of pump 24. Filter 18 surrounds the pump 24 and the outlet 25 of the pump 24 to filter particulates from gas extracted from the flue 13.

Sensor unit 20 includes a number of interconnected electronic elements including gas sensors 31-33 and temperature sensor 35. Housing 19 has a wall 8 that separates the filter 18 from electronic components of sensor unit 20. In some embodiments, wall 8 has a gas permeable membrane adjacent to openings in temperature sensor 35 and gas sensors 31-33. In other embodiments, wall 8 connects via conduit 27 to a manifold 28 which feeds filtered flue gas to temperature sensor 35 and gas sensors 31-33. The flue gas sample enters openings in the sensors 31-33, 35 and the sensors output analog signals. ADC 41 receives the analog sensor signals and converts them to digital signals. ADC 41 outputs digital sensor signals to microprocessor 40 and/or memory 42.

Microprocessor 40 may be programmed to perform a number of supervisory functions, analysis and other operations. Microprocessor 40 has a clock and may perform one or more operations based on sensed events, elapsed time between events or at periodic intervals. Microprocessor 40 is connected to an ADC 41 that converts analog output signals of the sensors into digital signals. Memory 42 holds data acquired by the sensors, in particular digital data from ADC 41 that are representative of the sensed temperature, gas type and gas concentration. Sensor transceiver 43 is connected to microprocessor 40. Sensor transceiver 43 may be a low power radio such as a Bluetooth Low Energy device. Transceiver 43 sends sensor data signals to wireless hand held gas analyzer unit 60 or central computer 70 or both and receives control signals from either or both the analyzer unit 60 and central computer 70.

In one embodiment, digital sensor signals are immediately transmitted by sensor transceiver 43 to wireless hand held gas analyzer unit 60 or to remote central computer 70. Sensor transceiver 43 also receives control signals from wireless hand held gas analyzer unit 60 or remote central computer 70. The control signals are output to microprocessor 40. The control signals may include commands to immediately sample and send digital data on current or stored digital signals representative of the temperature and the gas identification and concentrations. Other control signals may request such digital signals be sent at periodic intervals such as once per day.

Power supply 44 supplies power to all the electronic elements and sensors, either directly or indirectly through other components. For clarity of illustration, FIG. 2 omits detailed connections of power supply 44 to the electrical components and sensors. A typical power supply 44 includes one or more batteries that may be replaced or recharged on a periodic basis. In alternate embodiments, a power supply may be any suitable AC converter that is coupled to an AC source for converting AC voltage into DC. A buck converter is an example of one such converter.

The sensor unit 20 is designed to conserve battery power. When no measurements of the gas sample are under way, the microprocessor 40 may be programmed to shut off power to pump 24 and to sensors 31-33, 35 and to other components to conserve power. Power may be further reduced to microprocessor 40 and memory 42 to a level sufficient to maintain data in memory 42. The level of power to sensor transceiver 43 may be reduced to keep sensor transceiver 43 minimally operative to receive command signals. Power is restored to one or more components in response to one or more command signals received by sensor transceiver 43 from units 60, 70 or other control units or at a programmed and predetermined time.

Pump 24 draws a sample of combustion gas 16 into tube 21. Filter 18 removes particulates from the sample gas and provides a filtered flue gas to gas sensors 31-33 and temperature sensor 35. Sensors 31-33 generate output analog signals representative of the type of gas detected and the concentration of each detected gas. Sensor 35 generates an output analog signal representative of the temperature of the filtered flue gas. The analog outputs of sensors 31-33 and 35 are received by ADC 41, converted to digital signals and sent to microprocessor 40, which then stores the digital signals in memory 42. In other embodiments, the digital signals may go directly to memory 42. The microprocessor 40 retrieves the digital signals of the gas identity, concentration, and temperature from memory 42 and outputs them to sensor transceiver 43 to send the digital signals to wireless hand held gas analyzer unit 60 or remote central computer 70.

Figure 3:
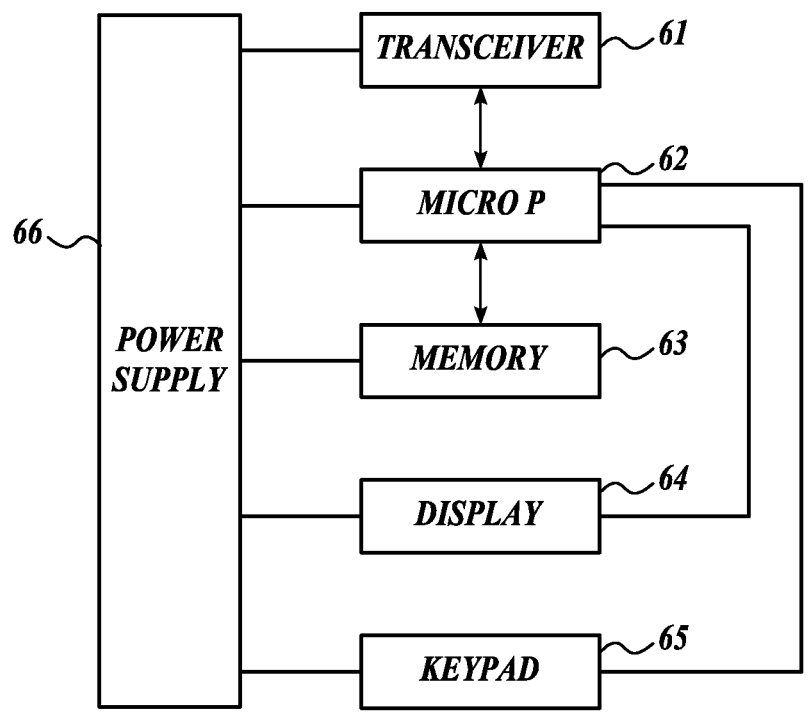
FIG. 3 is a schematic representation of one embodiment of a hand held unit control unit.

Wireless hand held gas analyzer unit 60, as shown in FIG. 3, includes transceiver 61, microprocessor 62, memory 63, display 64, keypad 65, and power supply 66. Transceiver 61 sends commands to sensor transceiver 43 and receives data signals from transceiver 43 representative of temperature, gas identity and concentrations of identified gases. The gas analyzer unit 60 may store received data signals in memory 63 or transmit such data to remote central computer 70.

Keypad 65 is used by a technician 15 to supply input data to microprocessor 62 and send control signals to sensor unit 20. Data input by keypad 65 may be stored in memory 63 or used to configure one or more commands for sensor unit 20. The system 10 may be set to continuously transmit data from sensor unit 20 to wireless hand held gas analyzer unit 60. During adjustment of the burner 12, continuous data from the sensor unit 20 is shown on display 64. The technician attending the burner 12 views display 64 while making adjustments to the fuel intake and air intake of the burner 12. By monitoring the resulting temperature, gases and concentrations of gases, technician 15 may optimize the efficiency and safety of the burner 12.

Power supply 66 supplies power to all the electronic elements and sensors, either directly or indirectly through other components. A typical hand held unit power supply 66 includes one or more batteries that may be replaced or recharged on a periodic basis. In alternate embodiments, a power supply may be any suitable AC converter that is coupled to an AC source for converting AC voltage into DC. A buck converter is one example of such a converter.

In some embodiments, the microprocessor 40 and memory 42 include circuitry and software disposed for processing output signals of the gas sensors 31-33 and the temperature sensor 35. In those embodiments, the hand held gas analyzer may be used for displaying the data processed by the microprocessor 40 and not for any further processing. In other embodiments, the hand held gas analyzer microprocessor 62 and memory 63 include circuitry and software disposed for processing output signals of the gas sensors 31-33 and the temperature sensor 35. In those embodiments, the hand held gas analyzer may be used for processing the digital output signals of the sensors as well as displaying the data captured by the microprocessor 40. In other embodiments, both the sensor unit 20 and the wireless hand held gas analyzer unit 60 have a microprocessor 40, 62 and memory 42, 63, respectively, for processing output signals of the gas sensors and the temperature sensor. In still further embodiments, the circuitry and software for analyzing the gases may be included in the central computer 70.

The embodiments are not limited to those described above and further embodiments are possible using knowledge of those skilled in the art for substituting and/or combining equivalent components that perform the same functions, in the same way to obtain the same results as disclosed above. For example, the probe 21 is a tube with a cylindrical cross section but may have other configurations. The memories 42, 63 are integrated into the respective microprocessors 40, 62. It is also contemplated that the ADC 41 may be incorporated into a single device with microprocessor 40. A digital signal processor may also replace the ADC 41 and microprocessor 40.

While illustrative embodiments have been illustrated and described, it will be appreciated that various changes can be made therein without departing from the spirit and scope of the invention.

The invention claimed is:

1. A gas analyzer system comprising:
a plurality of remote sensor units attachable to one more flues;
a hand held unit in communication with the plurality of remote sensor units; and
a host computer in communications with the plurality of remote sensor units,
wherein each remote sensor unit comprises:
a housing;
an elongated sampling tube extending from the housing and configured to have one end pass through a wall of a flue into a bore of the flue;
a pump having an inlet and an outlet, the inlet disposed at the other end of the sampling tube for drawing a sample of cumbustion gas from the flue into the housing;
one or more gas sensors in fluid communication with the outlet of the pump, said one or more gas sensors configured to sense a presence of one or more gases in the combustion gas and to measure a concentration of the one or more gases in the combustion gas;
a temperature sensor for sensing a temperature of the sample of combustion gas; and
a wireless transceiver coupled to receive measurement data obtained by the one or more gas sensors and the temperature sensor for sending signals representative of temperature, types of gases, and concentrations of gases to both the hand held unit and the host computer and to receive control signals, from both the hand held unit and the host computer;
wherein the hand held unit comprises:
a wireless transceiver for receiving signals representative of temperature, types of gases, and concentrations of gases from the remote sensor units and for transmitting control signals to one or more of remote sensor units; and a display that shows the temperature, types of gases, and concentrations of gases;

wherein circuitry and software disposed in one or both of the remote sensor units and the hand held unit, in operation, process output signals of the one or more gas sensors and the temperature sensor;

wherein the host computer comprises:

a wireless transceiver for receiving signals representative of temperature, types of gases, and concentrations of gases from the remote sensor units and for transmitting control signals to one or more of the remote sensor units;

a display that shows the temperature, types of gases, and concentration of gases; and circuitry and software that, in operation, process signals received from the remote sensor units and send control signals to one or more of the remote sensor units; and wherein at least one remote sensor unit wirelessly sends signals representative of temperature, types of gases, and concentration of gases in a flue to the hand held unit which allows a technician operating the hand held unit to make adjustments to a fuel intake and/or air intake of a burner coupled to the respective flue, and also wirelessly sends signals representative of temperature, types of gases, and concentration of gases in the flue to the host computer for review by an analyst reviewing combustion information in the respective flue and other flues that exhaust gas from other burners.

2. The system of claim 1, further comprising a filter disposed between the outlet of the pump and the one or more gas sensors.

3. The system of claim 1 wherein a remote sensor unit has one or more analog to digital converters for converting signals of the one or more gas sensors from analog signals to digital signals.

4. The system of claim 3 wherein the remote sensor unit has circuitry and software that process the digital signals and provide the digital signals to the wireless transceiver of the remote sensor unit for transmission to the hand held unit.

5. The system of claim 3 wherein the hand held unit has circuitry and software that process the digital signals and provide the control signals to the wireless transceiver of the hand held unit for transmission to the remote sensor unit.

6. The system of claim 1 wherein the control signals include a control wake up signal, a control sleep signal, and a control signal to set one or more times for the remote sensor units to transmit signals representative of temperature, types of gases, and concentrations of gases.

7. A wireless sensor for analyzing gases, the wireless sensor comprising:

a housing;

an elongated sampling tube extending from the housing and configured to have one end pass through a wall of a flue into a bore of the flue;

a pump having an inlet and an outlet, the inlet disposed at the other end of the sampling tube for drawing a sample of combustion gas from the flue into the housing;

at least one sensor in fluid communication with the outlet of the pump for sensing a parameter of the sample of combustion gas, wherein the parameter includes at least one of temperature, types of gases, and concentrations of gases in the combustion gas; and a wireless transceiver coupled to the at least one sensor for sending signals representative of the temperature, types of gases, and concentrations of gases to both a hand held unit and a host computer, and for receiving control signals from both the hand held unit and the host computer.

8. The wireless sensor for analyzing gases of claim 7 wherein the at least one sensor comprises one or more gas sensors in fluid communication with the outlet of the pump, said one or more gas sensors being configured to sense a presence of one or more gases in the combustion gas and to measure a concentration of one or more gases in the combustion gas.

9. The wireless sensor for analyzing gases of claim 7 wherein the at least one sensor comprises a temperature sensor for sensing the temperature of the sample of combustion gas.

10. The wireless sensor for analyzing gases of claim 8 wherein the at least one sensor comprises a temperature sensor for sensing the temperature of the sample of combustion gas.

11. The wireless sensor for analyzing gases of claim 7 wherein the sensor has circuitry and software for responding to control signals to wake up, to go to sleep, and to periodically transmit signals representative of temperature, types of gases and concentrations of gases.

12. A method for analyzing combustion gas in a flue, the method comprising:

providing, at each remote location of a plurality of remote locations, at least one gas sensor configured to sense a presence of one or more gases in a sample of combustion gas and to measure a concentration of the one or more gases in the combustion gas;

providing, at said plurality of remote locations at least one temperature sensor for sensing a temperature of the sample of combustion gas;

placing, at each remote location, one end of an elongated sampling tube into a bore of the flue;

pumping a sample of the combustion gas from the flue to the at least one gas sensor and the at least one temperature sensor; and wirelessly sending signals representative of temperature, types of gases, and concentrations of gases to both a hand held unit and a host computer, and wirelessly receiving control signals from both the hand held unit and the host computer.

13. The method for analyzing combustion gas in a flue of claim 12, further comprising:

at both the hand held unit and the host computer, wirelessly receiving the signals representative of temperature, types of gases, and concentrations of gases and wirelessly transmitting control signals;

displaying the temperature, types of gases, and concentrations of gases at both the hand held unit and the host computer; and generating control signals at both hand held unit and the host computer to operate the at least one gas sensor and the at least one temperature sensor at each remote location.

14. The method for analyzing combustion gas in a flue of claim 12, further comprising generating control signals to operate the at least one gas sensor and/or the at least one temperature sensor at each remote location to wake up, go to sleep, or periodically wirelessly transmit signals representative of temperature, types of gases, and concentrations of gases at one or more times.

15. The method for analyzing combustion gas in a flue of claim 12, further comprising:

continuously wirelessly sending signals representative of temperature, types of gases, and concentrations of gases in the flue, and wirelessly receiving control signals from the hand held unit which allows a technician operating the hand held unit makes adjustments to a fuel intake and/or air intake of a burner coupled to the respective flue; and further wirelessly sending signals representative of temperature, types of gases, and concentrations of gases in the flue to the host computer for review by an analyst reviewing combustion information in the respective flue and other flues that exhaust gas from other burners.

\* \* \* \* \*